United States Patent [19]

Barrows

[11] Patent Number: 4,534,349
[45] Date of Patent: Aug. 13, 1985

[54] ABSORBABLE SUTURELESS NERVE REPAIR DEVICE

[75] Inventor: Thomas H. Barrows, Cottage Grove, Minn.

[73] Assignee: Minnesota Mining and Manufacturing Company, St. Paul, Minn.

[21] Appl. No.: 569,557

[22] Filed: Jan. 12, 1984

Related U.S. Application Data

[63] Continuation-in-part of Ser. No. 436,242, Feb. 2, 1983, abandoned.

[51] Int. Cl.³ .............................................. A61B 17/04
[52] U.S. Cl. .............................. 128/334 R; 128/334 C
[58] Field of Search ......................... 128/334 R, 334 C

[56] References Cited

U.S. PATENT DOCUMENTS

| | | | |
|---|---|---|---|
| 3,937,223 | 2/1976 | Roth | 128/325 |
| 3,960,152 | 6/1976 | Augurt et al. | 128/335.5 |
| 4,033,938 | 7/1977 | Augurt et al. | 260/78.3 R |
| 4,074,366 | 2/1978 | Capozza | 3/1 |

Primary Examiner—C. Fred Rosenbaum
Assistant Examiner—C. W. Shedd
Attorney, Agent, or Firm—Donald M. Sell; James A. Smith; Lorraine R. Sherman

[57] ABSTRACT

Medical devices for the sutureless repair of lacerated, severed, or grafted nerves comprising longitudinally-openable, porous, rough-surfaced tubes of a body-absorbable polymer are disclosed. The tubular devices of the invention are prepared by sintering or otherwise bonding together granules or fibers, or melt processing suitable polymers in the form of the desired device.

11 Claims, 14 Drawing Figures

ABSORBABLE SUTURELESS NERVE REPAIR DEVICE

This is a continuation-in-part of application Ser. No. 436,242 filed Feb. 2, 1983 now abandoned.

DESCRIPTION

TECHNICAL FIELD

This invention relates to medical devices useful for the repair of injured nerves, to methods for the preparation of these devices, and to methods for using these devices in repairing nerves.

BACKGROUND ART

The repair of lacerated or severed peripheral nerves using sutures is a common surgical procedure known as neurorrhaphy. The use of this sophisticated technique in recent years has enhanced the surgeon's ability to replant amputated body parts, to achieve composite tissue transfer, and to graft nerves. The success of such procedures is still limited because the current method of suturing severed nerves is difficult, time-consuming, and often yields poor functional results due to a variety of factors.

The increased trauma created by surgical manipulation and suturing is especially problematic in repairing nerves since trauma stimulates the formation of intraneural and extraneural connective tissue. Invasion of the repair or anastomotic site by connective tissue in turn prevents the regenerating axons in the proximal stump from entering the microscopic tubules contained in the distal stump. If a substantial number of axons are prevented from crossing the anastomotic site, neuroma (painful nerve cell tumor) formation often results. In addition, prospects for achieving significant reinnervation are reduced. The end result is lack of full return of motor and/or sensory function.

Recognition of this problem has prompted many researchers to explore alternatives to direct suturing in nerve repair and a variety of approaches involving the use of many different types of materials have been experimented with over the past 100 years.

All of these alternatives to direct suturing seek to protect the anastomotic site by wrapping, tubulizing, or otherwise encasing it with a natural or foreign substance, either absorbable or nonabsorbable. Since accurate alignment of the nerve stumps is important, most of these methods of treatment still require the use of some sutures which therefore reduces their effectiveness.

Sutureless tubulization techniques are known to be successful only in the case of very small, single fascicle nerves. The saphenous nerve in rats (0.3–0.5 mm diameter) was transected and repaired with a preformed tube or single leaf of collagen membrane as disclosed by J. M. Rosen, E. N. Kaplan, D. L. Jewett, and J. R. Daniels, "Fascicular Sutureless and Suture Repair of the Peripheral Nerves, A Comparison Study in Laboratory Animals", *Orthopaedic Review* 8 (4), 85 (1979). This method of repair avoids sutures but requires a totally tensionless situation to avoid retraction of the nerve stumps. J. M. Rosen in *Orthopedic Transactions* 6(1), 75(1982) reports that the peroneal nerve in rats (0.5–1.2 mm in diameter) was transected and repaired with a thin-walled, extruded tube of polyglycolic acid, cut open longitudinally along one wall. This method also requires a totally tensionless situation and is not advisable in the case of larger nerves since the tight fit required to maintain adequate nerve stump approximation would not provide for the release of pressure created by post-surgical swelling. The loose fit to accommodate swelling is an important feature of commercially available Silastic TM nerve cuffs, which must be used in combination with sutures (Bulletin: 14-393, Medical Products Division, Dow Corning Corp., Midland, Mich. 48640, April, 1969). Moreover, as shown in Example 6 below, longitudinally-split, extruded, smooth tubing used in sutureless repair on a 1.5 mm diameter rat sciatic nerve was found to be unsatisfactory due to retraction of the nerve.

Another approach to sutureless tubulization involves sucking the nerve stumps into a porous, metallic tube by means of a complex, vacuum actuated instrument, disclosed in U.S. Pat. Nos. 3,916,905 and 3,960,151. This method also risks the causing of compressive injury to the nerve upon post-surgical swelling in addition to the disadvantage of preventing the surgeon from observing the anastomotic site to ascertain correct rotational alignment.

A further example of avoiding sutures at the anastomotic site of nerve repair is provided by the use of "human fibrin glue" applied to the separated fascicles of a transected rat sciatic nerve positioned in the grooves of a metallic plate, disclosed by R. Ventura, et al., *Ital. J. Orthop. Traumatol.* (Italy) 6, (3) 407–414 (1981). In this case, the protective effect of the metal is present on only one side of the nerve. Moreover, the fibrin glue alone was not shown to be sufficient to prevent nerve stump retraction since the nerve stumps were anchored to the metal plate with epineural sutures.

Examples of tubulization materials that have been used in combination with sutures include silicone rubber as taught by R. D. Midgley and F. M. Woolhouse, "Silicone Rubber Sheathing as an Adjunct to Neural Anastomosis, *Surgical Clinic of North America* 48, 1149 (1968), and collagen as disclosed by D. G. Kline and G. J. Hayes, "The Use of a Resorbable Wrapper for Peripheral Nerve Repair, Experimental Studies in Chimpanzees", *J. Neurosurgery* 21, 737 (1964). Silicone has the disadvantages of being impermeable and nonabsorbable whereas the disadvantage of collagen is its potential antigenicity.

R. L. Reid, D. E. Cutright, and J. S. Garrison, "Biodegradable Cuff an Adjunct to Peripheral Nerve Repair: A Study in Dogs", U.S. Army Institute of Dental Research, Walter Reed Army Medical Center, Government Report ADA044491, Aug. 29, 1977, also published in *The Hand* 10, (3) 259 (1978), disclose the use of the biodegradable copolymer poly(glycolide-co-lactide), as smooth, rigid tubes for use as nerve cuffs. These authors were unable to show any improvement with the use of this device. Sutures were used in both control and experimental groups since the device was not capable of providing a sutureless repair. Hakan Molander et al., "Regeneration of Peripheral Nerve through a Polyglactin Tube", *Muscle and Nerve* 5, 54–57 (1982), reported less than satisfactory results in bridging nerve defects (missing portions of nerves) by use of a biodegradable polyglactin suture mesh shaped as a tube around the defect to serve as a framework for proliferating cells.

U.S. Pat. No. 3,937,223 teaches a partially-compressed, heat-embossed, flexible, tissue-absorbable, compacted, surgical hemostatic felt having specific fiber and density measurements which is in the form of a thin conformable mat.

Two related patents, U.S. Pat. Nos. 4,033,938 and 3,960,152, disclose bioabsorbable polymers of unsymmetrically substituted 1,4-dioxane-2,5-diones which are broadly stated in col. 9, lines 29-31 and in the bridging paragraph of cols. 9 and 10 ('938) and in col. 9, lines 20-23 and lines 51-65 ('152) to be useful as tubes or sheets for surgical repair such as nerve and tendon splicing. A similar disclosure in U.S. Pat. No. 4,074,366, col. 6, lines 13-16 and 43-57, relates to poly(N-acetyl-D-glucosamine), i.e. chitin. However, there is no enabling disclosure in the specifications or in their Examples as to how such tubes are to be prepared, the characteristics required, and their method of use.

None of these references teaches a body-absorbable, porous, rough-surfaced device which is in the form of a longitudinally-openable tube which can be utilized for repair of a nerve without the use of sutures.

SUMMARY OF THE INVENTION

There remains a need, which is satisfied by the present invention, for a body-absorbable, protective nerve repair device that is tissue compatible, inhibits neuroma formation, rapidly achieves adequate fixation without the use of sutures, accommodates post-surgical swelling, and provides an optimum environment for normal nerve regeneration.

The present invention provides a device for the sutureless repair of a lacerated or severed nerve comprising a longitudinally-openable, porous, rough-surfaced tube of a natural or synthetic absorbable polymer such as those listed in TABLE I, below. Synthetic absorbable polymers are preferred because they are thermoplastic and when fibers or granules thereof are heated they become sintered and adhere together. They are also more conveniently dissolved in organic solvents which provide another method of bonding. Copolymers or mixtures of suitable polymers are also included within the scope of suitable materials. The tubular devices of the invention are prepared by sintering or otherwise bonding together granules or fibers, or melt processing suitable polymers in the form of the desired device.

TABLE I

A. Natural Polymers (1) Partially oxidized cellulose surgical hemostats (see U.S. Pat. No. 3,364,200) such as Oxycel TM (fibrous surgical hemostatic material, Parke-Davis) and Surgicel TM (woven fabric hemostatic material, Surgikos). These fibers can be cut to short lengths, formed into a nonwoven web, and bonded or stiffened by treatment with a solution of polylactic acid or other suitable synthetic bioabsorbable polymer dissolved in a solvent.

(2) Chitin and/or chitin derivatives in fibrous form treated as above (e.g. U.S. Pat. No. 4,074,366).

(3) Collagen, regenerated collagen, or catgut suture material, also processed as above in fibrous form.

(4) Natural polymers are preferably used in admixture with synthetic polymers.

B. Synthetic Polymers (1) Polyamino acids, polyamino acid copolymers and derivatives such as partially esterified poly-L-glutamic acid (U.S. Pat. No. 3,371,069), amino acid-hydroxy acid copolymer (U.S. Pat. No. 3,773,737), and nylon 2/nylon 6 copolymer (W. J. Bailey, et. al., "Biodegradable Polyamides", *Proceedings of 3rd International Biodegradation Symposium*, Sharpley and Kaplan, eds., Applied Science Publishers Ltd., London, 1976, p. 765-773).

(2) Polyesters formed from diols and succinic and/or oxalic acid such as U.S. Pat. Nos. 4,032,993 and 3,883,901, isomorphic copolyoxalates (U.S. Pat. No. 4,141,087), and poly(alkylene oxalates) (U.S. Pat. No. 4,140,678).

(3) Polymalic acid (U.S. Pat. No. 4,265,247).

(4) Polydioxanone (U.S. Pat. No. 4,052,988).

(5) Poly-beta-hydroxy acids such as polyhydroxybutyrate (U.S. Pat. No. 3,225,766).

(6) Poly-alpha-hydroxy acids such as polyglycolic acid, polylactic acid, copolymers of lactic and glycolic acids, and said polymers copolymerized with other polyesters (U.S. Pat. No. 4,118,470).

(7) Polymers made from unsymmetrically-substituted 1,4-dioxane-2,5-diones (U.S. Pat. No. 3,960,152).

(8) Polyesteramides such as U.S. Pat. Nos. 4,209,607 and 4,343,931.

The use of these devices in the method of the invention comprises selecting a device which is a longitudinally-openable and preferably is a split tube of suitable size to be used with the nerve stumps to be connected, placing the nerve stumps in one part of the longitudinally-openable tube and positioning the second part of the tube to form a closed, essentially cylindrical tube which holds the nerve stumps together.

The texture and porosity of the tube formed are such that the nerve stumps are held in place without irritation and within sufficient proximity that a high percentage of repairs show good reinnervation without the intrusion of excess connective tissue or neuroma formation.

The device of the present invention is a longitudinally-openable, porous tube having a rough inner surface that may be a unitary tube having one longitudinal slit therethrough or it may be a tube that has been divided into at least two portions by having at least two slits therethrough. It is envisioned within the scope of the present invention that portions of any one tube may have varying lengths and thicknesses.

In the present application:

"sutureless repair" means that stumps of lacerated, severed, or grafted nerves can be approximated and maintained in approximation without the use of sutures until healing commences and during the healing process;

"body absorbable" or "absorbable" means that the polymer is metabolized by the body and ultimately eliminated therefrom or used therein;

"porous" means the material contains void spaces or pores which communicate between the inner and outer surfaces. The interstitial pore size may vary widely, generally from about 1 micron up to about 1000 microns, although it may be preferred to use pore sizes in the range of about 100 to 500 microns. The porosity also may vary widely, generally from about 25% by volume to the limit of coherence (for example, 95% by volume) of the porous surface, and usually in the range of about 30 to about 95% by volume;

"rough surface" means that the device exhibits, at least on its inside surface, a coefficient of static friction, $\mu_s$, against a Whatman TM no. 1 filter paper surface, in the range of 0.40 to 0.90, preferably 0.50 to 0.80, wherein $$\mu_s = \tan \theta^{max}$$

and $\theta$ is the angle of inclination, and $\theta^{max}$ is the angle at which a test specimen begins to slide down a plane (i.e. angle of slip).

"tube" means a hollow elongated cylinder or a hollow channeled structure in which the hollow portion in cross-section is approximately circular, elliptical, U-shaped, V-shaped, trough-shaped with flat or curved bottom, or any variation of such shape. The shape of the tube may vary widely; the rough surface and porosity of the tube are the critical features;

"openable tube" means either a one-piece, longitudinally split, flexible tube or a tube comprising more than one part that can be flexible or rigid;

"longitudinally split tube" means a tube having at least a single slit; preferably it is a tube selected from an open tube having a integrally-attached cover such that it forms a living hinge and an open tube with a separate cover; and most preferably it is an open tube with a separate cover;

"flexible" means self-supporting and non-drapable, yet pliant so that bending through an arc of at least 45° does not cause fracture;

"rigid" means non-pliant so that bending through an arc of 45° results in fracture;

"axons" means filamentous extensions of nerve cells, capable of regeneration (elongation) upon cutting, which carry electrical impulses to and from the extremities; and "reinnervation" means nerve endings have reestablished connection so that muscle control and sensory function is restored.

BRIEF DESCRIPTION OF THE DRAWING

In the accompanying drawing which illustrates the invention.

DETAILED DESCRIPTION OF THE INVENTION

The absorbable devices of the present invention are longitudinally-openable tubes made by either impregnating a nonwoven web of body-absorbable fibers or body-absorbable woven fabric with a solution of a body-absorbable, thermoplastic binder polymer, evaporating the solvent, and thermoforming and cutting the web into the desired shape, or by sintering or otherwise bonding together granules or fibers of one or more absorbable polymers or copolymers in a mold or die. One portion of the longitudinally-openable tube or tubes serves as a tray on which the ends of severed or lacerated nerves can be placed for approximation without retracting. The proximal stump of the severed nerve is laid in the lower portion of the openable tube. The distal stump is then positioned in the lower portion of the openable tube so that it butts against the proximal stump. This alignment is accomplished atraumatically by grasping the adventitia or outer covering with a jeweler's forceps to manipulate the nerve. Rotational alignment is guided by noting the fascicular (bundlelike) and superficial vascular (blood-vessel-containing) patterns of each stump. The second part of the openable tube is then positioned on top of the first part to form a closed tube with a hollow central core which may be essentially cylindrical, elliptical, U-shaped, or having another shape previously described, and which encloses, holds, and protects the nerve stumps. It is preferred to use a tube having a configuration that closely approximates the shape of the nerve in order to maximize contact with the nerve to better prevent retraction.

The openable tube of the invention acts as a fixation tray since its rough surface prevents nerve retraction which might otherwise create a gap in the anastomotic site. The upper portion of the openable tube is placed over the lower portion to form a complete tube which contains the nerve anastomosis. The two portions need not be lashed together with suture since the nerve becomes bonded to the porous surface. Exudate from the nerve stumps coagulates after soaking into the porous tube thereby causing the nerve to become firmly attached to the device. This is especially noticeable when the device is completely dry during application.

Severance of a nerve generally results in retraction of the nerve stumps and reapproximation requires some level of tension to be exerted on the stumps. The device of the present invention with its rough surface overcomes some of the problems of prior art devices by allowing repair of nerves which are under a slight amount of tension.

Figure 1:
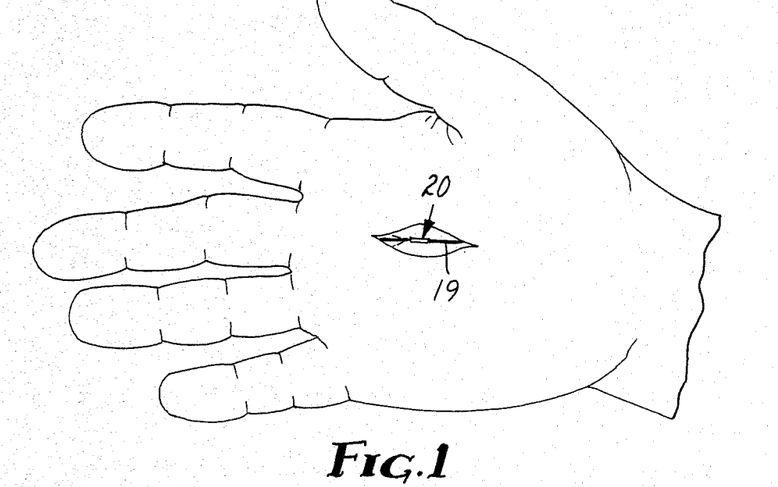
FIG. 1 is a human hand showing the invention in place surrounding a portion of a nerve.

Referring to the accompanying drawing, FIG. 1 shows the absorbable nerve repair device 20 of the present invention positioned about a portion of the palmer digital branch of median nerve 19 in the hand of a human patient.

Figure 2:
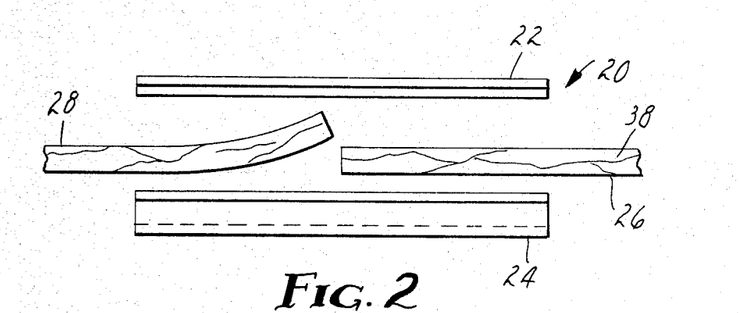
FIG. 2 is an exploded side view of a severed nerve being positioned in a split tube of the invention.
Figure 3:
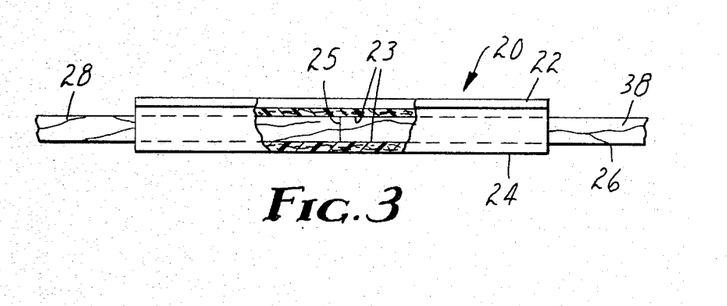
FIG. 3 is a side view of the split tube of FIG. 2, parts thereof broken away and shown in section.
Figures 4, 5:
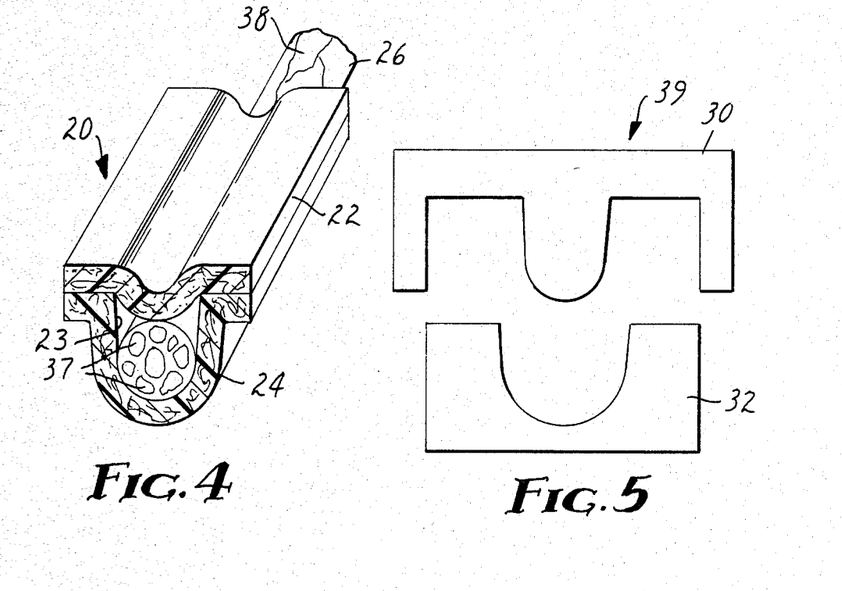
FIG. 4 is a partial perspective view of the embodiment shown in FIG. 3.
FIG. 5 is an end view of a die for making the bottom portion of the embodiment of FIG. 4.

FIGS. 2 and 3 show the split tube device 20, having lipped convex-shaped upper portion 22 and lipped U-shaped lower portion 24. In FIG. 2 severed nerve stumps 26 and 28 are shown before the stump ends are abutted and prior to being aligned and positioned in split tube device 20. FIG. 3 shows split tube 20 acting as a fixation device since its rough surface 23 prevents nerve retraction which might otherwise create a gap in the anastomotic site 25. FIG. 4 shows the nerve repair device having a lipped-U-shaped lower portion 24 and a lipped-convex-shaped upper portion 22 holding nerve 26 in position. Rotational alignment of the nerve stumps is guided by noting fascicular 37 and vascular 38 patterns of each stump. FIG. 5 is a die 39 for making the lipped-U-shaped lower portion 24 of the device of FIG. 4. Shown is upper portion 30 and lower portion 32 of die 39.

Figure 6:
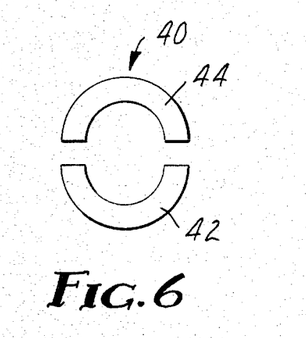
FIG. 6 is an end view of a modified split tube for holding a nerve, a second embodiment of the invention.
Figure 7:
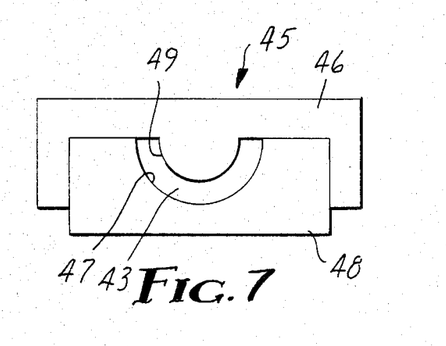
FIG. 7 is an end view of a die for making either portion of the embodiment of FIG. 6.

FIG. 6 shows an end view of a modified split tube 40, a second embodiment of the invention having identical lower portion 42 and upper portion 44. A die 45 for making either portion 42 or 44 of the device of FIG. 6 is shown in FIG. 7, and is further described in Example 4, below.

Figures 8, 9:
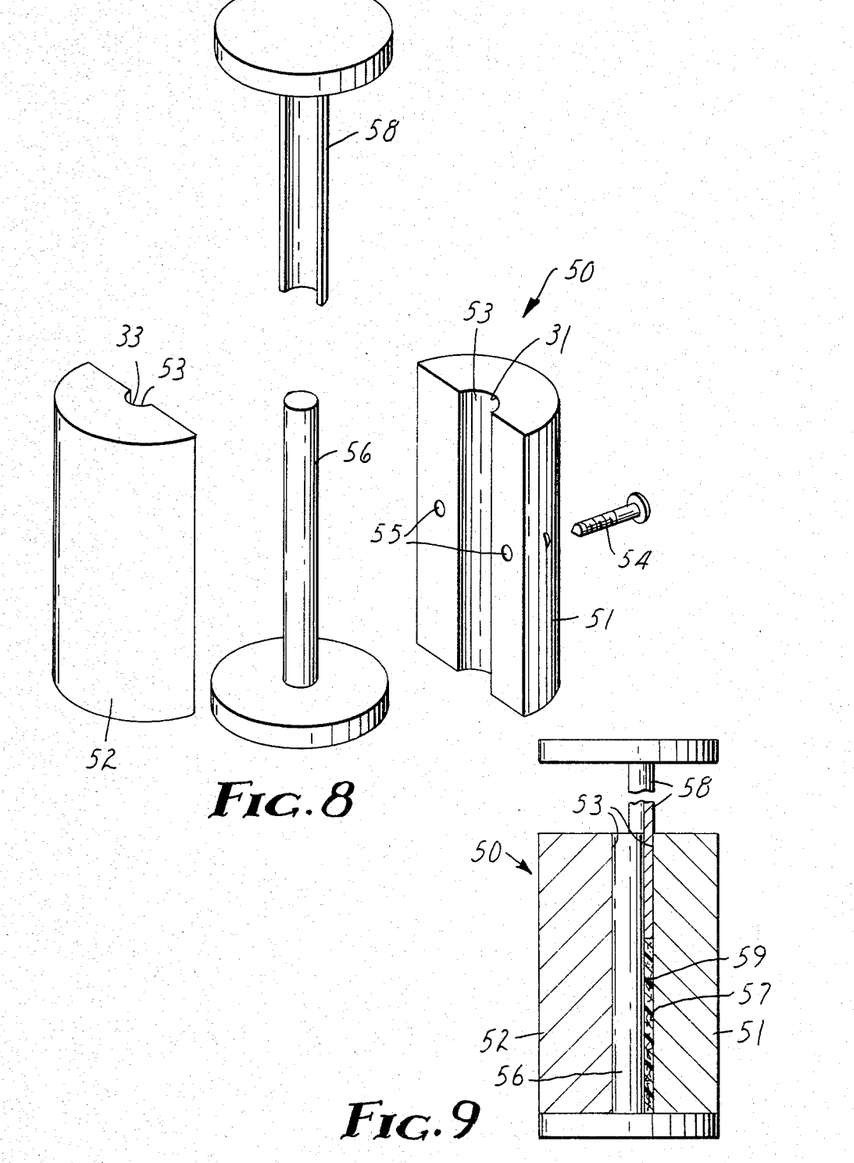
FIG. 8 is an exploded perspective view of a second means for making a split tube as shown in FIG. 6.
FIG. 9 is a cross-sectional view of FIG. 8 showing a tamping means in use.

A second means for making the split tube device of FIG. 6 is shown in FIGS. 8 and 9. Longitudinally split mold 50 has cylindrical halves 51 and 52 having central cylindrical bore 53. In use, cylindrical halves 51 and 52 are held together by screws 54 inserted through holes 55, or they may be held together by other fastening means such as binder bands. Shaft 56, when placed in cylindrical bore 53, produces cavity 57 having the shape of lower portion 42 or upper portion 44 of the split tube device. Tamping device 58 is used to compact polymer particles 59 that fill the cavity. The filled, closed mold is then heated to sinter particles 59 into a portion of the device of the invention.

Figure 10:
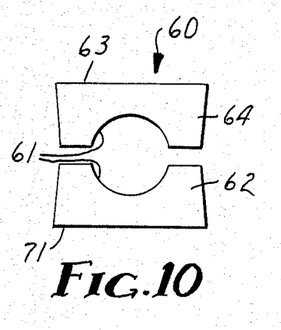
FIG. 10 is an end view of a modified split tube for holding a nerve, a third embodiment of the invention.
Figure 11:
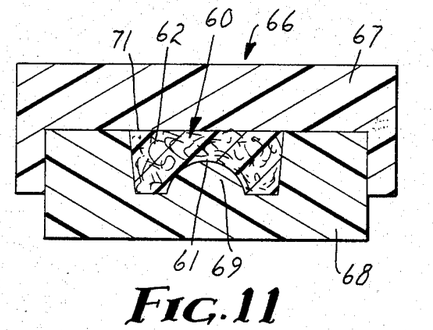
FIG. 11 is a sectional view of the die for making either portion of the embodiment of FIG. 10.

FIG. 10 shows an end view of a third embodiment 60 of the invention, with both the lower portion 62 and upper portion 64 being identical. This embodiment is further described in Example 2, below. FIG. 11 shows a die 66 for making either portion 62 or 64 of the split tube device of FIG. 10. Shown is upper portion 67 and lower portion 68 of die 66 with portion 62 of split tube 60 formed therein.

Figure 12:
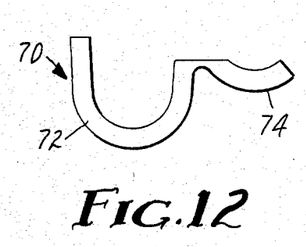
FIG. 12 is an end view of a modified open tube for holding a nerve, a fourth embodiment of the invention.

FIG. 12 shows a fourth embodiment 70 of the invention having open tube portion 72 and cover portion 74. Cover portion 74, which is integrally-attached, can be folded over to enclose an injured nerve which can be positioned in open tube portion 72.

Figure 13:
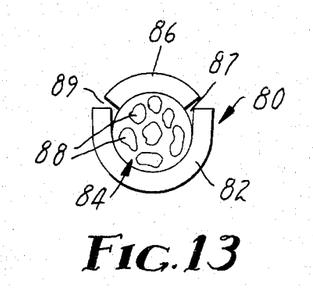
FIG. 13 is an end view of a modified split tube for holding a nerve, a fifth embodiment of the invention with the bottom portion being U-shaped and the top portion being in the shape of an arc.

A fifth embodiment 80 of the invention is shown in FIG. 13. U-shaped lower portion 82 holds injured nerve 84. Arc-shaped cover portion 86 securely positions nerve 84, yet allows for expansion of nerve tissue at apertures 87 and 89 if swelling occurs as the nerve heals. Fascicular pattern 88 is seen in the cut end of nerve 84.

The method of using the nerve repair device of the invention, described above, was employed using a tubular device prepared according to the procedure of EXAMPLE 1 below, with excellent results in the repair of a branch of the sciatic nerve in a large rat. The rat was reoperated on five weeks post-implantation of the nerve repair device. At this time the nerve responded to the same voltage of electrical stimulation as before transection. The tube was encapsulated and showed no evidence of an adverse reaction. Histologically, numerous axons had traversed the anastomotic site and excess connective tissue was absent. The implant was extremely well tolerated by the surrounding tissue.

The tube parts, in one preferred embodiment, were prepared from poly[oxysuccinoyloxydodecane-1,12-di(amidocarbonylmethylene)-co-10 percent-oxysuccinoyloxy-4,9-dioxadodecane-1,12-di(amidocarbonylmethylene)] granules sized to 212 to 250 microns by passage through one sieve and collection on a finer sieve. The granules were packed in a die which was then heated to sinter the tube part. The resultant part was self-supporting and possessed sufficient strength to withstand gentle handling without crumbling. Two such parts form a tube which is suitable for enclosing nerve stumps or damaged nerves.

Suitable polymers and copolymers for use in the device of the present invention are any polymer or copolymer in (a) woven or nonwoven fibrous form stiffened with a binder polymer or bonded together by heating, or (b) particulate form which may be sintered or otherwise bonded together, to give a porous structure in the device of the invention, the porosity being low enough so that encapsulation tissue cannot adhere to the anastomotic site, yet high enough so that fluids important for nutrition of the healing nerve can freely pass through the walls of the tube. The texture of the device is uneven enough to give a rough surface which prevents retraction of the aligned nerve stumps. Either absorbable or nonabsorbable polymers can be used, but it is preferred to use an absorbable polymer or copolymer, or mixtures of absorbable polymers or copolymers, since absorption of the device will avoid late complications that might otherwise occur with the use of a nonabsorbable device. The split tube design permits continuous visibility of the anastomotic site during the alignment procedure which is accomplished rapidly with standard instruments. This design also prevents deleterious compression of the nerve that might otherwise occur with a continuous tube during post-surgical swelling and edema since the two halves can separate slightly to release such pressure.

Preferred polymers and copolymers are polylactic acid (U.S. Pat. No. 3,636,956), polyglycolic acid (U.S. Pat. No. 3,297,033), polydioxanone (U.S. Pat. No. 4,052,988), poly(lactide-co-glycolide) (U.S. Pat. No. 4,137,921) and poly(esteramides) such as poly(oxysuccinoyloxydodecane-1,12-di(amidocarbonylmethylene)-co-10 percent-oxysuccinoyloxy-4,9-dioxadodecane-1,12-di(amidocarbonylmethylene) and poly[oxysuccinoyloxyhexane-1,6-di(amidocarbonylmethylene)] (U.S. Pat. No. 4,343,931), and mixtures thereof. These polymers and copolymers are preferred because they are known to be well tolerated by the body upon implantation in addition to being absorbable. Mixtures of polymers allow for variation of properties of tubes as described in Example 4.

Body-absorbable, thermoplastic, binder polymers used to stiffen woven or nonwoven fibrous polymeric materials in the present invention include polylactic acid and polyesteramides such as poly(oxysuccinoyloxydodecane-1,12-di(amidocarbonylmethylene)-co-10 percent-oxysuccinoyloxy-4,9-dioxadodecane-1,12-di(amidocarbonylmethylene), poly[oxysuccinoyloxyhexane-1,6-di(amidocarbonylmethylene)] and other polyesteramides disclosed in U.S. Pat. No. 4,343,931. Solvents useful with these binder polymers include acetone for polylactic acid and 2,2,2-trifluoroethanol for polyesteramides.

Both the staple fiber size and particle size of polymers used in fabricating the device and wall thickness of the device depend to a certain extent upon the size of the nerve to be repaired. Since the device is intended for use with all peripheral nerves, the internal diameter can vary from approximately 10.0 mm to 0.1 mm. Alternatively, large nerves can be dissected apart to permit repair of single fascicles or groups of fascicles separately, each with an appropriately sized tubulization device. Polymer particles that are between 212 microns (0.0083 inches) and 250 microns (0.0098 inches) across are useful in preparing tubes that have a 1.0 to 2.0 mm inside diameter and a wall thickness of 0.3 to 0.6 mm. Staple fiber can vary from 10 to 150 microns in diameter and from 1 to 10 mm in length. It has been found that particles and fibers of this size range produce devices with adequate strength and porosity when sintered. The devices must possess sufficient strength to withstand handling without crumbling. Tubes larger than 2.0 mm in diameter (i.e., up to 10 mm in diameter) will generally require a wall thickness up to 25 percent of the inside diameter. Tubes with an inside diameter of less than 1.0 mm (tubes with an inside diameter of 0.1 mm are envisioned as being useful and are within the scope of this invention) may still require a minimum wall thickness of 0.3 mm but may be made from particles much finer than 212 microns (0.0083 inches). The use of staple fibers is especially advantageous in preparing devices for use with small nerves since wall thickness of 0.3 mm or lower can be achieved. The surface roughness, achieved by varying the particle or fiber size and utilizing sintering or bonding conditions, may be decreased with decreasing nerve size since the forces required to prevent nerve stump retraction also decrease proportionally. Greater surface roughness results when bonding or sintering takes place under lower temperatures and using larger sized particles or fibers. The length of the tube will generally be from 5 to 15 mm, longer tubes being used with larger nerves and shorter tubes being used with smaller nerves and in specialized situations.

In order to sinter the polymers or copolymers useful in the devices of the invention, the granules are packed by gentle tamping into a mold or die as shown in FIGS. 8 and 9 and heated just hot enough and long enough so that the particles are firmly bonded but not agglomerated. The exact time and temperature of such a successful sintering process depend on the softening point of the polymer and the dimensions and composition of the mold. Alternatively, a bonding agent such as a lower melting polymer may be added to the granules in powdered or dissolved form. This is especially useful in the case of high melting, difficult-to-sinter polymers such as polyglycolic acid. Polylactic acid serves as an excellent bonding polymer for polyglycolic acid. Other thermoplastic binder polymers include polyesteramides. Upon heating the mixture, or evaporation of the solvent, a porous network of bonded granules useful in the present invention is obtained.

In order to fabricate polymers or copolymers into nonwoven or woven devices of the invention, a dissolved thermoplastic binder polymer is applied to a wet- or dry-laid web of fiber staple or woven fabric of the desired polymer. The solvent is then evaporated from the web or fabric which is then thermoformed and cut into the desired shape.

In a preferred process, a solvent or mixture of solvents such as halogenated solvents, e.g., 1,1,1,3,3,3-hexafluoro-2-propanol for polyglycolic acid, chloroform for polylactic acid, or 2,2,2-trifluoroethanol for polyesteramides, is applied to granules or fibers of a bioabsorbable polymer in an amount and at a temperature sufficient to make the surface of the polymer tacky. In the case of 1,1,1,3,3,3-hexafluoro-2-propanol and polyglycolic acid a useful temperature range is 20° to 25° C. The solvent-treated polymer is formed or molded into the desired shape and remaining solvent is evaporated without increasing the temperature. The resultant tube may be flexible if formed from fibrous polymer or it may be rigid if formed from granular polymer. The tubes are suitable for use as a nerve repair device according to the method of the present invention.

The tubes have been prepared as described, for example, in Examples 1, 2, 3, and 4 below by using molds which provide symmetrical half tubes, but other alternatives are available as described, for example, in Examples 5, 6, and 7 in which the walls of the split tube extend upward to form a U-shaped cross-section. This latter design gives greater confidence in the security of the anastomosis but requires fabrication of a cover which circumscribes less than 180 degrees of a circle. Alternatively, tubes described in Examples 5, 6, and 7 can be closed with lids such as the lipped-convex-shaped upper portion 22 of device 20 shown in FIG. 4, that are placed over the anastomosis with convex side down.

The ability of devices of this invention to prevent nerve stump retraction is surprisingly good and appears to be due to the combination of surface roughness and porosity. It is believed that the tube "wicks" fluid away from the surface of the nerve thereby enhancing the integrity of the interaction between the nerve and the tube surface. Furthermore, as mentioned above, exudate from the nerve stumps coagulates after soaking into the porous tube thereby causing the nerve to become firmly attached to the device. This is especially noticeable when the device is completely dry during application. On the other hand, the nerves are not so firmly entrapped in the device that significant tension can be produced, for example, to bridge a large gap due to removal of a segment of the nerve. Indeed, it is poor surgical technique to attempt to bridge a gap by producing tension since a better result is obtained by nerve grafting. The process of nerve grafting is greatly simplified by use of the tubulization device which should promote greater utilization of the grafting procedure.

Methods of preparing rigid or flexible, porous, split tubes without the use of granules or fibers are encompassed by this invention. For example, the polymer can be dissolved in a solvent in the presence of a leachable filler (such as a high melting water-soluble salt such as NaCl, or a high melting water-soluble organic compound such as glycine) which is subsequently leached out to create the porous structure, the method being described in Example 1 of U.S. Pat. No. 4,355,426. Alternatively, the polymer can be melt processed in the presence of a leachable filler to achieve a similar result.

Objects and advantages of this invention are further illustrated by the following examples, but the particular materials and amounts thereof recited in these examples, as well as other conditions and details, should not be construed to unduly limit this invention.

EXAMPLE 1

A. Device Fabrication

Poly[oxysuccinoyloxydodecane-1,12-di(amidocarbonylmethylene)-co-10 percent-oxysuccinoyloxy-4,9-dioxododecane-1,12-di(amidocarbonylmethylene)] was synthesized by the method described in U.S. Pat. No. 4,343,931 and was obtained as porous particles ranging in size from 3 to 5 mm in diameter to a fine dust. The granules were sized by passage through a No. 60 sieve [250 microns (0.0098 in.) openings, W. S. Taylor, Inc. Mentor, OH 44060] and collection on a No. 70 sieve [212 microns (0.0083 in.) openings]. The granules were carefully packed into a specially machined mold illustrated in FIGS. 8 and 9. The mold was made from metal cut in half longitudinally and fastened back together with screws 54 such that one side 31 of the bore was 1.8 mm in diameter and the other side 33 of the bore 53 was 1.2 mm in diameter. A 1.2 mm diameter shaft 56 was then placed inside the bore 53 to produce a cavity 57 with the desired dimensions. The cavity 57 was filled with polymer particles 59 using a 1.2 mm inner diameter, 1.8 mm outer diameter split tube as a tamping device 58. The filled mold was then heated at 180° C. for 30 minutes to sinter the particles. Upon cooling, the polymeric part was removed by first extracting the solid 1.2 mm shaft 56 and then pushing on the sintered polymer granules 59 with the tamping device 58. This process was then repeated to obtain the second half of the tubulization device.

B. Evaluation

Male Sprague-Dawley strain rats were anesthetized with ketamine hydrochloride and acepromazine maleate. An incision was made over the sciatic nerve and the nerve isolated by blunt dissection. The nerve was transected and repaired in one trial with the tubular device of EXAMPLE 1 by positioning the nerve stumps together in one of the split tubes and placing a second split tube on top to complete the tubulization. This was accomplished in a matter of seconds and retraction of the nerve stumps was not a problem since the epineurium clung to the dry, porous surfaces of the device. In another trial, nerve repair was attempted by wrapping the nerve stumps with a 0.5 mil (12.7 microns) thick piece of extruded film made of the same polymer. This method was unsatisfactory because the film became slippery when moist and the nerve stumps retracted. Two additional nerve repairs were performed with suture as controls. The incisions were closed with skin clips and the rats were returned to their cages.

After five weeks, the rats were reoperated on and nerve function assessed by electrical stimulation using a Grass Model S8 Stimulator (Grass Medical Instruments, Inc.). With frequency set at 1 cps and duration at 1 msec., the voltage was slowly increased until a muscle contraction distal to the anastomosis occurred. The sutured and tubilized nerves responded to electrical stimulation, whereas the poorly repaired, film-wrapped nerve was unresponsive.

EXAMPLE 2

A. Device Fabrication

Polylactic acid was synthesized from dl-lactide as follows: 1 kg of lactide (Clinton Corn Processing Co., Clinton, Iowa 52732) was recrystallized from 4 liters of ethyl acetate and dried at 60° C. under vacuum to give 535 g of pure lactide. The pure lactide (485 g) was placed in a 1 liter flask with 10 drops of stannous octanoate catalyst and heated with stirring under nitrogen in an oil bath to 180° C. The increase in viscosity soon prevented further stirring. The flask was heated at 180° C. for 1 hour and then allowed to cool. The product was collected by breaking the flask and cleaving the hard, glassy polymer into small pieces. Inherent viscosity was found to be 1.21 (0.5 percent in $CHCl_3$ at 30° C.).

The polymer was processed into small particles by feeding thin, melt-pressed sheets into a Waring TM blender (Waring Products Division, Dynamics Corporation of America, New Hartford, CT 06065). The particles were sized with the use of sieves as in EXAMPLE 1 and sintered in Teflon TM molds at 160° C. for approximately 5 minutes. The molds in this case, shown in FIG. 11, were channels cut in the surface of a Teflon TM block to produce a trough-shaped lower portion 68 of die 66 with a central ridge 69 that was hemispherical in cross-section. As is shown in FIG. 10, two molded parts matched together to form a tube with a cylindrical bore 61 and a flat top 63 and bottom 71. In order to provide a selection of tube sizes, molds were prepared to give parts with inside diameters of 1.20, 1.35, 1.50, 1.65, and 1.80 mm.

B. Evaluation

Sixteen male rats weighing between 450 and 542 grams were anesthetized by injection with sodium pentobarbital. An incision was made over the right sciatic nerve and the nerve isolated by blunt dissection. Two rats had the sciatic nerves cut with no repair of any kind. These served as negative controls. Three rats had their transected sciatic nerves repaired with 9-0 size nylon suture (Dermalon TM, Davis-Geck, American Cyanamid Co., Pearl River, NY 10965) using standard microsurgical technique. These rats served as positive controls. Eleven rats had their transected nerves repaired using the above polylactic acid tubes. The tubes were either 1.35 or 1.50 mm in diameter and were shortened to 10 mm at the time of implantation by gently breaking off excess length. Using the technique described in EXAMPLE 1, the tubulization method of repair was rapid and adequately secure. The incisions were closed with skin staples and the rats returned to their cages.

After six weeks, surgery was performed on the rats to examine the site of nerve repair. The first two rats with unrepaired nerves were noted to have ulcerations of the right foot and missing toes. In both cases no connection or growth of the nerve was observed under the operating microscope. The distal ends of these nerves were biopsied for histological evaluation.

All three of the rats with sutured nerves had ulcerations of the right foot and missing toes. One of these rats had a definite neuroma at the anastomotic site and gave no muscle response upon cutting the nerve. The other two rats did respond to this mechanical stimulation.

Of the eleven rats with tubulized nerves six had ulcerations of the right food and missing toes and five showed no missing toes or skin changes on their right feet. In all cases the two tube halves were together about the nerve and the implants were well tolerated by the surrounding tissue. The tubes and small segments of nerve proximal and distal to the anastomosis were removed for histological examination by first cutting proximal to the tube and then distal to the tube. Upon making these cuts, the leg was observed for signs of muscle contraction caused by mechanical stimulation of the nerve. In all cases, both cuts stimulated motion of the foot and withdrawal of the leg.

Histologically, the two nonrepaired nerve specimens showed complete Wallerian degeneration whereas all repaired nerve sections showed the presence of significant amounts of myelin and large numbers of axons distal to the repair site. Two of the nerves repaired by tubulization were examined by transmission electron microscopy which showed substantial regeneration of both myelinated and unmyelinated axons.

EXAMPLE 3

A. Fabrication of Drug-Releasing Device

The drug cis-hydroxy-L-proline (CHP) has previously been shown to reduce neuroma formation when administered systemically by inhibiting the synthesis of collagen. (J. M. Lane, F. W. Bora, and D. Pleasure, "Neuroma Scar Formation in Rats Following Peripheral Nerve Transection", *The Journal of Bone and Joint Surgery* 60-A:2, 197, March, 1978). Since it is known that polylactic acid is useful for dispensing drugs (see U.S. Pat. No. 3,887,699), additional tubulization devices were prepared from CHP-containing polylactic acid to determine the effect on nerve regeneration.

Polylactic acid containing either 1 percent or 5 percent CHP was prepared from the polymer of EXAMPLE 2 by dissolving the polymer in acetone and adding a small volume of aqueous CHP with rapid mixing. This caused CHP to precipitate as a fine powder. The solvent was then rapidly evaporated under reduced pressure and the resultant solid dried under vacuum at 60° C. The 1 percent and 5 percent CHP-polylactic acid mixtures were then fabricated into split tubes according to the method described in EXAMPLE 2.

B. Evaluation

Thirteen male rats weighing 516 to 538 grams were anesthetized by injection with sodium pentobarbital. An incision was made over the right sciatic nerve and the nerve isolated by blunt dissection. Two rats had 1 percent CHP tubes of inner diameter 1.5 mm applied to their intact nerves as controls. Eight rats had their transected nerves repaired with 1 percent CHP tubes and three had nerves repaired with 5 percent CHP tubes. The incisions were closed with skin staples and the rats returned to their cages.

After six weeks, surgery was performed on the rats to examine the site of nerve repair. The two rats with intact nerves had normal feet with no signs of paralysis. The tubes were removed and analyzed for residual CHP content. By comparing this value with the value obtained from pre-implantation controls, it was estimated that 260 micrograms of CHP per 1 percent CHP tube was released during the implantation period. Sections of these control nerves from within the tubes were examined histologically and found to be perfectly normal, thus confirming that the tube and CHP do not cause adverse reactions.

Of the remaining eleven rats with repaired nerves, three had normal feet with no missing toes. All but two exhibited motion of the foot and withdrawal of the leg upon cutting the nerve proximal and distal to the anastomosis. Histological examination of these specimens showed the presence of nerve regeneration beyond the site of repair.

The incorporation of CHP into the polymer did not seem to have an effect on the results. This is most likely due to the fact that neuroma formation, a common problem with the suture method of repair, is not a problem with the tubulization method of repair of the present invention.

EXAMPLE 4

Polyglycolic acid was synthesized from glycolic acid using a procedure similar to the one described by Gilding and Reed (*Polymer* 20, 1459, December 1979). A one liter round bottom flask equipped with a thermometer, distillation apparatus, motor driven mixer, and nitrogen inlet and outlet was charged with 581 g of high purity glycolic acid (Eastman Kodak Co., Rochester, NY 14650) and heated to 140° C. by means of an electric heating mantle. As distillation of water subsided the temperature of the melt was gradually increased to a maximum of 220° C. with stirring and dry nitrogen sweep. The distillation apparatus was then connected to a vacuum pump and the heating continued under high vacuum. Distillation of glycolide occurred as the temperature reached 225° to 270° C. Under these conditions, however, a large portion of the residue was converted into a carbonaceous solid. The distillate was ground to a powder upon solidification and extracted twice with chloroform to remove the yellow color. The product was then recrystallized twice from ethyl acetate and dried in vacuo to yield 96.3 g of white, lustrous crystals. The crystalline glycolide was then placed in a 500 ml round bottom flask equipped with a motor driven mixer and nitrogen inlet and outlet. Approximately 0.04 g of stannous octanoate catalyst (K & K Laboratories, Inc., Plainview, NY) was added and the mixture was rapidly heated to 200° C. under nitrogen with stirring by immersion of the flask into a preheated oil bath. After about 10 minutes the viscosity increased to the point that stirring was no longer possible. The flask was heated at 220° C. for a total of 20 minutes and then allowed to cool to room temperature whereupon the glass flask shattered. The brown, glassy polymer was cleaved into small pieces and freed of glass particles. The polyglycolic acid was then processed into small particles by feeding thin, melt pressed sheets into a Waring TM blender.

A two piece Teflon TM mold was designed to produce thin walled split tubes. As shown in FIG. 7, the bottom half 48 of mold 45 had a centrally located channel 47 in which a centrally located ridge 49 on the top half 46 of mold 45 fitted such that a semi-circular gap 43 of 0.3 mm existed when the two halves were mated together. The gap formed the mold cavity which was used to produce one split tube part.

Polylactic acid prepared as in EXAMPLE 2 was dissolved in chloroform to give a 17.8 percent (w/v) solution. This solution was mixed with polyglycolic acid powder (less than No. 70 sieve size particles) as needed to produce a stiff, paste-like consistency. The bottom half of the above mold was filled with this mixture and the top half of the mold pressed down into the mixture and moved back and forth several times to expel excess material from between the two halves. The top half was removed and excess material on the face of the bottom half of the mold scraped off. The mold thus filled was placed in an oven at 160° C. for about 15 min. Upon cooling, the bottom portion of a longitudinally split tube with inside diameter of 1.50 mm and outside diameter of 2.1 mm and having a dull, porous surface on all sides was easily removed from the Teflon TM mold. The molded part had adequate strength and, by using a 5 cm long mold, was broken into four or five segments for subsequent use in tubulization neurorrhaphy.

The use of polylactic acid as an adhesive for the much higher melting polyglycolic acid particles was especially advantageous since it obviated the need for precise heating conditions required in the sintering process.

EXAMPLE 5

Figure 14:
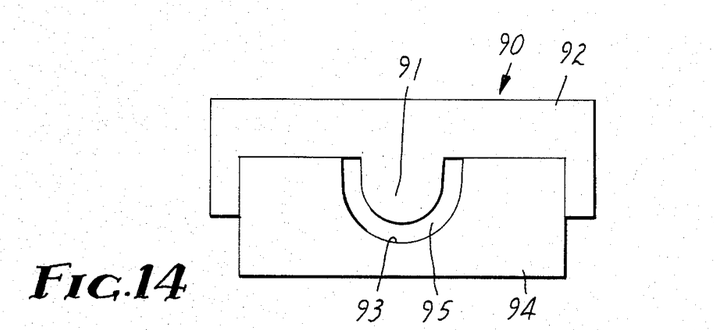
FIG. 14 is an end view of a die for making the bottom portion of the embodiment of FIG. 13.

A two piece Teflon TM mold was designed similar to the one used in EXAMPLE 4. As shown in FIG. 14, this mold 90 differed from the EXAMPLE 4 mold in that the ridge 91 on the upper portion 92 of the mold 90 protruded into a deeper channel 93 in the lower portion 94 of the mold 90 while maintaining a gap 95 of 0.3 mm. The gap was used as a mold cavity to produce a deep channeled open tube as shown in FIG. 13. This molded part had an inside radius of 0.75 mm and an inside depth of 1.25 mm.

Polyglycolic acid granules from EXAMPLE 4 were sized by passage through a No. 70 sieve (212 microns, 0.0083 in.) and collected on a No. 100 sieve (150 microns, 0.0059 in.) and mixed with a 15 percent (w/v) solution of polylactic acid, prepared as in EXAMPLE 2, in acetone. The mixture was placed in the cavity of the bottom half of the above-described mold and the top half pressed firmly in place. The mold thus filled and assembled was placed in an oven at 180° C. for 15 minutes and then allowed to cool to room temperature. The part was then ejected from the mold and trimmed of excess material at the part line. Covers for these parts were prepared by using the device of EXAMPLE 4 and cutting them approximately in half lengthwise. FIG. 13 shows a cross-sectional view of this device 80 with nerve 84 and cover 86 in place.

The advantage of using a split tube that accommodates more than one half of the nerve circumference is that it provides better holding power during the initial nerve stump alignment step of the tubulization procedure.

EXAMPLE 6

A. Device Fabrication

Braided polyglycolic acid suture (Dexon TM U.S.P. size No. 1, Davis and Geck, American Cyanamid Co., Pearl River, NY 10965) was carefully unraveled and cut into lengths of approximately 5 to 10 mm. The resultant microfiber staple was thoroughly stirred in a solution of 15 percent (w/v) polylactic acid, prepared as in EXAMPLE 2, in acetone. This mixture was then placed in a Buchner funnel and the excess solution removed by suction to produce a loose, fibrous mat. After evaporation of residual acetone, a strip of material cut from the center of the fibrous mat was placed in the mold of EXAMPLE 5, heated in an oven at 180° C. for 10 minutes and then allowed to cool while the mold halves were held together with gentle pressure. Upon removal from the mold and trimming excess material, a U-shaped lower portion of a device part similar to the one shown in FIG. 13 was obtained. The lower portion of the device was sufficiently rigid and porous and had the advantage compared to the device of EXAMPLE 5 of a thinner wall and a stronger, more resilient construction.

B. Evaluation

Smooth-surfaced extruded tubing (outside the scope of the present invention) was compared with the rough-surfaced tubing of the invention prepared in this Example.

Two male Sprague-Dawley strain rats were anesthetized with ketamine hydrochloride and acepromazine maleate. An incision was made over the sciatic nerve and the nerve isolated by blunt dissection. The nerve was transected and repaired in one case with the above device by positioning the nerve stumps together in the trough and covering it with a piece cut from the same material that is less than one half circle in cross-section as shown in FIG. 13. This was accomplished easily and retraction of the nerve stumps was not a problem.

In the second rat, the nerve was transected and repair attempted by placing the nerve stumps inside a 1 cm piece of 1.57 mm inside diameter, 2.08 mm outside diameter polyethylene tubing (Intramedic TM, Becton-Dickinson Co., Rutherford, NJ). The tube was first cut open longitudinally and spread apart by an assisant while the surgeon manipulated the nerve stumps into the tube. The tendency of the cut tubing edges to spring back together hampered the task of accurate nerve approximation. Moreover, the smooth tubing offered no resistance to retraction and the nerve stumps, once approximated, repeatedly slipped apart. This situation was aggravated by the accumulation of fluid between the nerve and the polyethylene.

The results showed that nerve repair using smooth-surfaced tubing was not achieved whereas nerve repair with the rough-surfaced device of the present invention gave a satisfactory result.

EXAMPLE 7

A. Device Fabrication

A 137 cm (54 in.) U.S.P. No. 2 Dexon TM "S", green braided polyglycolic acid suture (Davis & Geck, Inc., Manati, PR 00701, USA) was cut into 3 to 6 mm lengths. The braided pieces were combined with 300 ml of distilled water and subjected to high shear mixing in a Waring TM blender which readily debraided and separated the individual micro fibers. The suspended fibers were collected on a wire screen and allowed to dry. The resultant web was carefully deposited on a piece of filter paper and gently soaked with 1,1,1,3,3,3-hexafluoro-2-propanol (99+%, Aldrich Chemical Co., Milwaukee, WI 53201) applied from a medicine dropper. The solvent was allowed to evaporate at room temperature in a well ventilated area to produce a bonded web that was flexible, yet stiff and self-supporting. The web weight was approximately 15 mg/cm$^2$ with a thickness of approximately 0.5 mm. Rectangular pieces were cut from the web and molded into U-shaped cross-section, open tubes using the type of mold described in EXAMPLE 5. The molding process was accomplished by rewetting the web with 1,1,1,3,3,3-hexafluoro-2-propanol, pressing it between the two mold halves, and allowing it to dry thoroughly. Trace residues of solvent were removed from the device by subjecting it to high vacuum for several days.

B. Evaluation

The above-described device, sized to accommodate a 4 mm diameter nerve, was sterilized with ethylene oxide. A flat piece of web for use as a cover was also sterilized. A 13 year old male pigtail monkey (Macaca nemistrina) was used for this evaluation. With the monkey under general anesthesia, an incision was made over the median nerve in the distal forearm using aseptic technique. The median nerve was supported by a sterile piece of wood and transected with a sharp blade. The nerve stumps were easily approximated in the U-shaped portion of the device which was then covered with a flat strip cut from the web. The skin was closed with sutures and the hand was placed in slight flexion and immobilized for 4 weeks in a cast.

At 3 months post operation the site of nerve repair was reoperated. The nerve was completely healed together with no gross evidence of abnormality or excessive scar formation. The nerve repair device was totally absorbed leaving no visible signs of foreign body reactions. Electrical stimulation of the nerve gave a compound action potential that was approximately 10% of normal, indicative of early nerve regeneration across the repair site expected after this elapsed healing time.

EXAMPLE 8

Poly[oxysuccinoyloxyhexane-1,6-di(amidocarbonylmethylene)] was synthesized according to the method disclosed in U.S. Pat. No. 4,343,931. The granular polymer was placed on a No. 100 sieve (149 micron openings) and the particles that passed through the sieve were placed in a 3.8 cm (1.5 in.) diameter steel die. The polymer was then subjected to a force of 592 kg/cm$^2$ (8,420 psi) for several minutes and removed from the die to yield an opaque, white, rigid wafer with a density of 0.876 g/cm$^3$. The material was 31.6 percent porous based on the density of 1.28 g/cm$^3$ measured from a solid sheet of the same polymer. The material was then heat treated at 170° C. for approximately 15 minutes to sinter the particles such that contact with moisture did not result in disintegration. The interconnecting porosity of this material was demonstrated by placing a drop of ink on the sample and observing that it was absorbed and wicked through to the opposite surface.

EXAMPLE 9

Granules of the polymer prepared in EXAMPLE 10 were sized by passage through a No. 25 sieve (710 micron openings) and collected on a No. 80 sieve (175 micron openings). The granules were mixed with a 10 weight percent solution of the same polymer dissolved in 2,2,2-trifluoroethanol. The damp mixture was then gently pressed into a 2 mm thick sheet and the solvent was allowed to evaporate. The resulting material had a coarse surface texture and a density of 0.322 g/cm$^3$ (74.8 percent porous).

EXAMPLE 10

A. Device Fabrication

A 137 cm (54 in.) U.S.P. No. 2 Dexon TM "S", green braided polyglycolic acid suture (Davis & Geck, Inc., Manati, PR 00701, USA) was cut into 3 to 6 mm lenghts. The braided pieces were combined with 300 ml of dichloromethane and subjected to high shear mixing in a Waring TM blender which readily debraided and separated the individual micro fibers. The suspended fibers were collected and allowed to dry. The resulting flock was then air-laid to form a web. The resultant web was carefully deposited on a piece of filter paper and gently soaked with a binder solution of 2 weight percent polyglycolic acid dissolved in 1,1,1,3,3,3-hexafluoro-2-propanol (99+%, Aldrich Chemical Co., Milwaukee, WI 53201) applied from a glass sprayer. The solvent was allowed to evaporate at room temperature in a well ventilated area to produce a circular bonded web that was flexible, yet stiff and self-supporting. The web weight was approximately 0.2845 g with a thickness of approximately 0.043 cm (0.017 in.) and a diameter of approximately 7.6 cm (3.0 in.). Rectangular pieces were cut from the web and molded into U-shaped cross-section, open tubes using the type of mold described in EXAMPLE 5. The molding process was accomplished by rewetting the web with 2 weight percent polyglycolic acid dissolved in 1,1,1,3,3,3-hexafluoro-2-propanol, pressing it between the two mold halves, and allowing it to dry thoroughly. Trace residues of solvent were removed from the device by subjecting it to high vacuum for several days.

EXAMPLE 11—surface roughness, density, and porosity

The surface roughness of the devices of EXAMPLES 2, 6, 7, 8, 9, and 10 and five controls (polyethylene, brass, Whatman TM no. 1 filter paper, 600 grit Wetordry TM sandpaper (3M), and 280 grit Wetordry TM sandpaper (3M, St. Paul, Mn)) was evaluated by determining the coefficient of static friction, $\mu_s$, which is defined above under the definition of "rough surface".

Test materials were mounted to the bottom of an 11.0 g brass cylinder (1.27 cm dia.×1.03 cm high) with transparent double stick tape (Scotch TM Double Stick Tape, 3M). The inclined plane was surfaced with reference material, i.e., Whatman no. 1 filter paper, by taping the edges of the paper to the inclined plane. The inclined plane was elevated at the rate of approximately 5°/sec. until the angle of slip was reached. Ten determinations were made for each test material. The results are shown in TABLE II below.

TABLE II

| Coefficient of friction test results from angle of slip measurements on Whatman TM no. 1 filter paper surface | | | |
|---|---|---|---|
| Sample | $\theta^{max}$ | Standard deviation | $\mu_s$ |
| Polyethylene | 16.0 | ±1.6 | 0.28 |
| Brass | 16.2 | ±2.6 | 0.29 |
| EXAMPLE no. 2 | 27.1 | ±2.3 | 0.51 |
| Whatman TM no. 1 Filter Paper | 28.7 | ±2.9 | 0.55 |
| EXAMPLE no. 8 | 31.7 | ±1.3 | 0.62 |
| EXAMPLE no. 6 | 32.2 | ±0.9 | 0.63 |
| EXAMPLE no. 7 | 35.4 | ±2.5 | 0.71 |
| EXAMPLE no. 9 | 38.4 | ±1.7 | 0.79 |
| EXAMPLE no. 10 | 42.0 | ±2.3 | 0.81 |
| 600 Grit Wetordry TM Sandpaper | 42.6 | ±1.6 | 0.92 |
| 280 Grit Wetordry TM Sandpaper | 52.4 | ±2.9 | 1.29 |

The data of TABLE II show that the devices of this invention have surface roughness greater than smooth materials such as polyethylene film, but not as great as fine sandpaper. Devices having coefficients of friction in the range of 0.40 to 0.90 are useful, with those having coefficients of friction in the range of 0.50 to 0.80 being preferred.

The observed density and calculated porosity data for the samples of EXAMPLES 2,6,7,8,9, and 10 are tabulated in TABLE III below.

TABLE III

| | Density and Porosity | |
|---|---|---|
| Sample material | Observed density (g/cm$^3$) | Percent porous |
| EXAMPLE 8 | 0.876 | 31.6 |
| EXAMPLE 2 | 0.578 | 54.5 |
| EXAMPLE 9 | 0.322 | 74.8 |
| EXAMPLE 7 | 0.300 | 76.4 |
| EXAMPLE 10 | 0.150 | 88.0 |
| EXAMPLE 6 | 0.105 | 91.7 |

The data TABLE III show the range of porosity exhibited by devices within the invention.

Varius modifications and alterations of this invention will become apparent to those skilled in the art without departing from the scope and spirit of this invention, and it should be understood that this invention is not to be unduly limited to the illustrative embodiments set forth herein.

I claim:

1. A medical device for use in the sutureless repair of a nerve comprising a longitudinally-openable, porous, rough-surfaced tube of at least one body-absorbable polymer, said tube having a porosity in the range of 25 to 95 percent by volume, a coefficient of static friction, $\mu_s$, in the range of 0.40 to 0.90, and being capable of enclosing, holding in approximation, and protecting the ends of a severed or lacerated nerve.

2. The device according to claim 1 wherein said polymer is selected from the group consisting of polylactic acid, polyglycolic acid, polydioxanone, poly(lactide-co-glycolide), polyesteramides, and copolymers and mixtures thereof.

3. The device according to claim 2 wherein said polymer is a mixture of polyglycolic acid and polylactic acid.

4. The device according to claim 1 wherein said polymer is in a form selected from the group consisting of (a) a web of non-woven fiber and (b) a woven fabric, said polymer being bonded by treatment with a solvent.

5. The device according to claim 4 wherein said polymer is polyglycolic acid in the form of a web and bonding is achieved by treatment with a solvent.

6. The device according to claim 4 wherein said polymer is polyglycolic acid in the form of a web and bonding is achieved by treatment with a polymer solution.

7. The device according to claim 1 wherein said device is comprised of bonded granules of said polymer.

8. The device according to claim 1 wherein said polymer is poly[oxysuccinoyloxydodecane-1,12-di(amidocarbonylmethylene)-co-10 percent-oxysuccinoyloxy-4,-9-dioxadodecane-1,12-di(amidocarbonylmethylene)].

9. The device according to claim 1 wherein said polymer is poly[oxysuccinoyloxyhexane-1,6-di(amidocarbonylmethylene)].

10. The device according to claim 1 wherein said tube has an inside diameter in the range of 0.1 to 10 mm.

11. The device according to claim 1 wherein said coefficient of static friction of said rough-surfaced tube is in the range of 0.05 to 0.80.

* * * * *

UNITED STATES PATENT AND TRADEMARK OFFICE
CERTIFICATE OF CORRECTION

Page 1 of 2

PATENT NO. : 4,534,349

DATED : August 13, 1985

INVENTOR(S) : Thomas H. Barrows

It is certified that error appears in the above-identified patent and that said Letters Patent is hereby corrected as shown below:

Title page:

Col. 2 the following references were omitted from the References Cited section of the patent:

3,916,905  11/75  Kuhn  128/334

3,960,151  6/76  Kuhn  128/334

Rosen, J.M., et al. "Fascicular Sutureless and Suture Repair of the Peripheral Nerves, A Comparison Study in Laboratory Animals" Orthopedic Review, 8 (4), P. 85, 1979

Rosen, J.M., "Sutureless Repair of Peripheral Nerves with P.G.A. Tubes in Rats", Orthopedic Transactions, 6 (1), P. 75 (1982)

Bulletin: 14-393, Medical Products Division, Dow Corning Corp., Midland, Michigan 48640, April 1969

Ventura, R. et al., Ital. J. Orthop. Traumatol. (Italy), 6, (3) 407-414 (1981) "Experimental Suture of the Peripheral Nerves with Fibrin Glue"

UNITED STATES PATENT AND TRADEMARK OFFICE
CERTIFICATE OF CORRECTION

Page 2 of 2

PATENT NO. : 4,534,349
DATED : August 13, 1985
INVENTOR(S) : Thomas H. Barrows

It is certified that error appears in the above-identified patent and that said Letters Patent is hereby corrected as shown below:

Midgley, R.D. and Woolhouse, F.M., Silicone Rubber Sheathing as an Adjunct to Neural Anastomosis", Surgical Clinic of North America, 48, 1149, 1968

Kline, D.G. and Hayes, G.J., "The Use of A Resorbable Wrapper for Peripheral Nerve Repair, Experimental Studies in Chimpanzees", J. Neurosurgery, 21, 737, 1964

Reid, R.L., Cutright, D.E. and Garrison, J.S., "Biodegradable Cuff an Adjunct to Peripheral Nerve Repair: A Study in Dogs", The Hand, 10, No. 3, (1978)

Molander, Hakan, et al., "Regeneration of Peripheral Nerve through a Polyglactin Tube", Muscle and Nerve, P. 54-57 (Jan. 1982)

Column 20, line 23, delete "0.05" and insert --0.50-- therefor.

Signed and Sealed this

Eighth Day of April 1986

[SEAL]

Attest:

DONALD J. QUIGG

Attesting Officer  Commissioner of Patents and Trademarks